United States Patent [19]

Davé et al.

[11] Patent Number: 4,899,006
[45] Date of Patent: Feb. 6, 1990

[54] PRODUCTION OF AROMATICS FROM ETHANE AND/OR ETHYLENE

[75] Inventors: Dilip Davé, London; Antony H. P. Hall, Cobham, both of England

[73] Assignee: The British Petroleum Company PLC, London, England

[21] Appl. No.: 309,440

[22] Filed: Oct. 7, 1981

[30] Foreign Application Priority Data

Oct. 11, 1980 [GB] United Kingdom ............... 8032910

[51] Int. Cl.$^4$ ..................... C07C 12/02; C07C 12/42
[52] U.S. Cl. ................................ 585/415; 208/135
[58] Field of Search ......................... 208/135; 585/415

[56] References Cited

U.S. PATENT DOCUMENTS 3,760,024 9/1973 Cattanach ..................... 585/415
4,350,835 9/1982 Chester et al. ................. 585/415

OTHER PUBLICATIONS

*J. Catalysis*, vol. 67, No. 1, Jan. 1981, V. Frilette et al, "Catalysis by Crystalline Aluminosilicates: Characterization of Intermediate Pore Size Zeolites by the 'Constraint Index'".

*Primary Examiner*—Curtis R. Davis
*Attorney, Agent, or Firm*—Brooks, Haidt, Haffner & Delahunty

[57] ABSTRACT

The invention relates to a process for producing aromatic hydrocarbons from a hydrocarbon feedstock rich in $C_2$ hydrocarbons. In particular it is a process for producing aromatic hydrocarbons comprising bringing into contact at a temperature between 580° C. and 750° C. a hydrocarbon feedstock containing at least 70% by weight of $C_2$ hydrocarbons with a catalyst composition comprising an aluminosilicate having gallium deposited thereon and/or aluminosilicate in which cations have been exchanged with gallium ions, said aluminosilicates containing silica to alumina in a molar ratio of at least 5:1. The process affords a one-step method of upgrading $C_2$ feedstock into aromatics.

11 Claims, No Drawings

PRODUCTION OF AROMATICS FROM ETHANE AND/OR ETHYLENE

The present invention relates to a process for producing aromatic hydrocarbons from a hydrocarbon feedstock rich in $C_2$ hydrocarbons.

Hitherto synthetic routes to producing aromatics from open chain hydrocarbons have started from feedstocks which have at least three carbon atoms. Such feedstocks are initially dimerised and the dimerised product is subsequently cyclised over a variety of catalysts at temperatures in the region of 500°–600° C. Such processes are described for example in our British Pat. Nos. 1507778 and 1561590.

It has now been found that aromatics may be produced from hydrocarbon feedstocks containing less than three carbon atoms.

Accordingly, the present invention is a process for producing aromatic hydrocarbons comprising bringing into contact at a temperature between 580° C. and 750° C. a hydrocarbon feedstock containing at least 70% by weight of $C_2$ hydrocarbons with a catalyst composition comprising an aluminosilicate having gallium deposited thereon and/or an aluminosilicate in which cations have been exchanged with gallium ions, said aluminosilicates containing silica to alumina in a molar ratio of at least 5:1.

The $C_2$ hydrocarbon in the feedstock may be ethane, ethylene or mixtures thereof. The feedstock may contain in addition other open chain hydrocarbons containing between 3 and 8 carbon atoms as coreactants. Specific examples of such additional coreactants are propane, propylene, n-butane, isobutane, n-butenes and isobutene. The hydrocarbon feedstock suitably contains at least 80% by weight of $C_2$ hydrocarbons.

The gallium in the catalyst composition may be present as gallium oxide and/or as gallium ions if cations in the aluminosilicate support have been exchanged with gallium ions. In the case where the cations in the aluminosilicate have been exchanged for gallium ions, the gallium ion is suitably provided as an aqueous solution of a gallium salt such as for instance gallium nitrate, gallium chloride or gallium sulphate. Such catalysts may be prepared by conventional ion exchange techniques and the catalysts so produced are subsequently dried. For example an aqueous solution of a gallium compound such as gallium nitrate may be placed in contact with the aluminosilicate at ambient or elevated temperature, eg by refluxing. The exchanged aluminosilicate is then separated by decantation followed by filtration, washed several times with deionised water and finally dried. Before addition to the aqueous solution of the gallium compound, the aluminosilicate may be treated in the manner described in our published copending European Patent Application No. 0024930.

The process of the present invention may also be carried out using catalysts in which the gallium deposited is impregnated on the surface of the aluminosilicate or is incorporated in the intracrystalline zeolite cavities as a gallium compound which gives rise to gallium oxide during activation of the catalyst prior to contact with the hydrocarbon feedstock. An example of a suitable gallium compound is gallium nitrate. Conventional impregnation techniques may be used to produce these catalysts.

The impregnation may be achieved by preparing a solution, suitably an aqueous solution, of a gallium compound such as for example gallium nitrate and adding a conventional aluminosilicate to this aqueous solution with thorough stirring to form a paste. The paste is subsequently dried at an elevated temperature in vacuum.

Where the catalyst composition is prepared by using a compound of gallium which ionises in aqueous solution, for example gallium nitrate, it is inevitable that some of the gallium ions will be exchanged with the cations in the aluminosilicate even if the preparation was by impregnation of the aluminosilicate.

The aluminosilicates which have gallium compounds deposited thereon and/or in which an exchange with gallium ions may be carried out suitably have a silica to alumina ratio of between 20:1 and 150:1 and may be selected from zeolites of the general formula: $M_{2/n}O.Al_2O_3.ySiO_2$ wherein M is a cation which is a positively charged ion selected from a metal ion or an organic ion of valence n and a proton, y is an integer greater than 5 and z is from 0 to 40. The metal cation, M, is preferably an alkali metal or alkaline earth metal ion, preferably sodium or potassium ions. The organic cations may be represented by the formula $R^1R^2R^3R^4N^+$ or by an ion derived from the amine $R^1R^2R^3N$, the diamine $R^1R^2N(CH_2)_xNR^3R^4$ or pyrrolidine where $R^1R^2R^3$ and $R^4$ may be H, $CH_3$, $C_2H_5$, $C_3H_7$, $C_4H_9$ or $-CH_2CH_2OH$ and x equals 2, 3 4, 5 or 6. The ZSM variety of zeolites, for example ZSM-5, ZSM-8, ZSM-11, ZSM-12 and ZSM-35 may be used and these are extensively described in a number of publications including U.S. Pat. No. 3970544 (Mobil). These zeolites are usually produced from a silica source, an alumina source, an alkali metal hydroxide and an organic nitrogen containing cation. However, the zeolite may also be derived directly using a nitrogen-containing base, instead of a cation, such as an alkanolamine, for example diethanolamine. Zeolites made in this manner are described in our published European Patent Application Nos. 0002899 and 0002900.

Whichever method of catalyst preparation is used, the amount of gallium present in the catalyst compositions may vary for instance between 0.05 and 10% by weight of the total aluminosilicate in the catalyst composition. The gallium exchanged or impregnated zeolite thus obtained may be combined with a porous matrix, e.g. silica or alumina or other inorganic compositions to improve the mechanical strength of the catalyst.

The catalyst composition may be activated prior to contact with the hydrocarbon feedstock. The activation may be carried out by heating the catalyst at a temperature of between 400° C. and 650° C., preferably between 500° C. and 600° C. Activation may be carried out in an atmosphere of hydrogen, air or a gas inert under the reaction conditions such as nitrogen but preferably in an atmosphere containing oxygen. The activation may be carried out in the reactor itself prior to the reaction. The catalyst composition is suitably used in a fixed bed, a moving bed or a fluidised bed.

The hydrocarbon feedstock is thereafter contacted in the vapour phase with the catalyst composition at a temperature between 580° and 750° C. preferably between 580° and 650° C. in an inert atmosphere in the absence of oxygen. The inert atmosphere may be provided by a gas inert under the reaction conditions such as nitrogen distillation. Any unreacted ethane or ethylene recovered from the reaction products may be recycled to the aromatisation reaction.

The invention is further illustrated with reference to the following Examples.

EXAMPLES 1-3

The catalyst used in these Examples was obtained by ion-exchanging a high silica zeolite having a silica to alumina ratio of 40:1, prepared in its hydrogen form, with gallium nitrate solution (0.05 g. Ga ml). The dry product was mixed with a silica binder, dried and sieved to 12 to 30 BSS mesh. The resulting catalyst contained 1.6% by weight of gallium and 29% by weight of the silica binder. 200 ml. of this catalyst was charged to a fixed bed reactor and air was passed over the bed at 550° C. for 2-3 hours. Thereafter the reactor was flushed with nitrogen for 0.5 hr to remove any traces of air. Ethane was then passed over this catalyst.

The reaction conditions used and the results achieved are shown below in Tables 1 and 2.

TABLE 1

AROMATISATION OF ETHANE.
Ga/High Silica Zeolite at 1 bar

| Example No. | Reaction Temperature (°C.) | Conversion of Ethane (%) | Yields (weight %) | |
|---|---|---|---|---|
| | | | Ethylene | Aromatics |
| 1 | 585 | 29.3 | 3.2 | 17.3 |
| 2 | 627 | 51.8 | 22.9 | 17.2 |
| 3 | 653 | 41.3 | 12.9 | 16.9 |

TABLE 2

PRODUCT DISTRIBUTION FROM AROMATISATION OF ETHANE

| Benzene | 30.2 weight % |
|---|---|
| Toluene | 41.8 weight % |
| $C_8$ | 9.0 weight % |
| $C_9$ | 5.0 weight % |
| Polycyclic Aromatics | 13.9 weight % |

We claim:

1. A process for producing aromatic compounds which comprises contacting under conversion conditions, a gaseous paraffinic hydrocarbon feed containing ethane, with a catalyst comprising gallium and a crystalline zeolite characterized by a constraint index within the approximate range of 2 to 8.7 and a silica to alumina ratio of at least 5, the weight of gallium in said catalyst being between about 0.05 to about 10 percent based on the total weight of catalyst whereby ethane present in said gaseous feed is converted to aromatic compounds, and recovering said aromatic compounds as liquids.

2. The process of claim 1 wherein said crystalline zeolite is selected from the group consisting of ZSM-5, ZSM-11, ZSM-12 and ZSM-35.

3. The process of claim 2 wherein said zeolite is an acid form.

4. The process of claim 1 wherein said zeolite is ZSM-5.

5. The process of claim 1 wherein said zeolite is ZSM-11.

6. The process of claim 1 wherein said zeolite is ZSM-12.

7. The process of claim 1 wherein said zeolite is ZSM-35.

8. The process of claim 1 wherein the concentration of gallium in said catalyst is about 1.6 percent by weight.

9. The process of claim 1 wherein said catalyst composition is composited with a porous matrix material.

10. The process of claim 1 wherein said catalyst composition is composited with a porous matrix material in a proportion of 11 percent by weight of catalyst composition in the dry composite.

11. The process of claim 1 wherein said zeolite is a HZSM-5 zeolite.

* * * * *